(12) United States Patent
Glukhovsky (10) Patent No.: US 7,492,935 B2
(45) Date of Patent: Feb. 17, 2009

(54) DEVICE, METHOD, AND SYSTEM FOR REDUCED TRANSMISSION IMAGING

(75) Inventor: Arkady Glukhovsky, Santa Clarita, CA (US)

(73) Assignee: Given Imaging Ltd, Yoqneam Ilite (IL)

(*) Notice: Subject to any disclaimer, the term of this patent is extended or adjusted under 35 U.S.C. 154(b) by 935 days.

(21) Appl. No.: 10/875,517

(22) Filed: Jun. 25, 2004

(65) Prior Publication Data

US 2005/0025368 A1    Feb. 3, 2005

Related U.S. Application Data

(60) Provisional application No. 60/482,456, filed on Jun. 26, 2003.

(51) Int. Cl.
*G06K 9/00* (2006.01)
(52) U.S. Cl. .................. 382/128; 382/232; 348/45; 348/65; 348/72; 375/240; 600/101
(58) Field of Classification Search .................. 382/128
See application file for complete search history.

(56) References Cited

U.S. PATENT DOCUMENTS

| | | | |
|---|---|---|---|
| 3,683,389 A | 8/1972 | Hollis | |
| 3,723,644 A | 3/1973 | Haskell et al. | |
| 3,971,362 A | 7/1976 | Pope et al. | |
| 4,149,769 A | 4/1979 | Zobel | |
| 4,278,077 A | 7/1981 | Mizumoto | |
| 4,689,621 A | 8/1987 | Kleinberg | |
| 4,741,327 A | 5/1988 | Yabe | |
| 4,844,076 A | 7/1989 | Lesho et al. | |
| 4,854,328 A | 8/1989 | Pollack | |
| 4,936,823 A | 6/1990 | Colvin et al. | |
| 5,098,426 A | 3/1992 | Sklar et al. | |
| 5,099,322 A * | 3/1992 | Gove .......................... 348/700 |
| 5,209,220 A * | 5/1993 | Hiyama et al. .............. 600/109 |
| 5,239,418 A | 8/1993 | Tyler et al. | |
| 5,247,357 A * | 9/1993 | Israelsen ................. 375/240.12 |

(Continued)

FOREIGN PATENT DOCUMENTS

DE    2941363    10/1979

(Continued)

OTHER PUBLICATIONS

Watkinson, J., "The MPEG Handbook: MPEG-1, MPEG-2, MPEG-4", 2001, ISBN: 0 240 51656 7, pp. 15-16 and 329-330.*

(Continued)

*Primary Examiner*—Matthew C. Bella
*Assistant Examiner*—Sath V. Perungavoor
(74) *Attorney, Agent, or Firm*—Pearl Cohen Zedek Latzer, LLP (57) ABSTRACT

An in-vivo device, system, and method are described where an in-vivo device may transmit an image stream to an external receiving device. Reducing the size of the image data necessary for transmission may conserve energy consumed by the in-vivo device during transmission. An image data comparator unit incorporated within the in-vivo device may compare a captured image to a previously transmitted image and transmit, for example, only captured images that are substantially dissimilar to a previously captured image.

28 Claims, 4 Drawing Sheets

U.S. PATENT DOCUMENTS

| | | | |
|---|---|---|---|
| 5,267,033 A | 11/1993 | Hoshino | |
| 5,272,530 A * | 12/1993 | Cassereau | 375/240.12 |
| 5,279,607 A | 1/1994 | Schentag et al. | |
| 5,331,551 A * | 7/1994 | Tsuruoka et al. | 382/128 |
| 5,379,757 A * | 1/1995 | Hiyama et al. | 600/109 |
| RE34,965 E | 6/1995 | Sugiyama | |
| 5,441,041 A | 8/1995 | Sauer et al. | |
| 5,477,858 A | 12/1995 | Norris et al. | |
| 5,539,466 A * | 7/1996 | Igarashi et al. | 375/240.15 |
| 5,551,947 A | 9/1996 | Kaali | |
| 5,569,292 A | 10/1996 | Scwemberger et al. | |
| 5,572,252 A | 11/1996 | Naka et al. | |
| 5,596,366 A | 1/1997 | Takashima et al. | |
| 5,604,531 A | 2/1997 | Iddan et al. | |
| 5,619,597 A * | 4/1997 | Moreton | 382/296 |
| 5,666,955 A | 9/1997 | Kondo et al. | |
| 5,681,260 A * | 10/1997 | Ueda et al. | 600/114 |
| 5,697,384 A | 12/1997 | Miyawaki et al. | |
| 5,738,110 A | 4/1998 | Beal et al. | |
| 5,754,700 A * | 5/1998 | Kuzma | 382/236 |
| 5,758,091 A * | 5/1998 | Hannah | 709/247 |
| 5,805,733 A * | 9/1998 | Wang et al. | 382/232 |
| 5,819,736 A | 10/1998 | Avny et al. | |
| 5,833,603 A | 11/1998 | Kovacs et al. | |
| 5,853,005 A | 12/1998 | Scanlon | |
| 5,864,366 A * | 1/1999 | Yeo | 375/240.12 |
| 5,873,830 A | 2/1999 | Hossack et al. | |
| 5,928,159 A | 7/1999 | Eggers et al. | |
| 5,993,378 A | 11/1999 | Lemelson | |
| 5,999,662 A | 12/1999 | Burt et al. | |
| 6,053,873 A | 4/2000 | Govari et al. | |
| 6,074,349 A | 6/2000 | Crowley | |
| 6,101,276 A * | 8/2000 | Adiletta et al. | 382/236 |
| 6,165,128 A | 12/2000 | Cespedes et al. | |
| 6,172,712 B1 | 1/2001 | Beard | |
| 6,184,922 B1 * | 2/2001 | Saito et al. | 348/65 |
| 6,228,030 B1 | 5/2001 | Urbano et al. | |
| 6,229,578 B1 | 5/2001 | Acharya et al. | |
| 6,240,312 B1 | 5/2001 | Alfano et al. | |
| 6,285,791 B1 * | 9/2001 | Bjorklund | 382/236 |
| 6,304,284 B1 | 10/2001 | Dunton et al. | |
| 6,346,940 B1 * | 2/2002 | Fukunaga | 345/427 |
| 6,366,186 B1 | 4/2002 | Hill et al. | |
| 6,428,469 B1 | 8/2002 | Iddan et al. | |
| 6,438,405 B1 | 8/2002 | Mooney et al. | |
| 6,519,353 B1 * | 2/2003 | Ogura | 382/107 |
| 6,546,276 B1 | 4/2003 | Zanelli | |
| 6,584,348 B2 | 6/2003 | Glukhovsky | |
| 6,587,711 B1 | 7/2003 | Alfano et al. | |
| 6,607,301 B1 | 8/2003 | Glukhovsky et al. | |
| 6,618,445 B1 * | 9/2003 | Peng et al. | 375/240.25 |
| 6,635,834 B1 | 10/2003 | Wenner | |
| 6,701,058 B1 * | 3/2004 | Tsubaki | 386/46 |
| 6,709,387 B1 * | 3/2004 | Glukhovsky et al. | 600/109 |
| 6,744,974 B2 | 6/2004 | Neuman | |
| 6,764,440 B2 | 7/2004 | Iddan et al. | |
| 6,898,313 B2 * | 5/2005 | Li et al. | 382/176 |
| 6,939,292 B2 * | 9/2005 | Mizuno | 600/118 |
| 6,951,536 B2 * | 10/2005 | Yokoi et al. | 600/128 |
| 7,085,424 B2 * | 8/2006 | Kajiki et al. | 382/239 |
| 2001/0017649 A1 | 8/2001 | Yaron | |
| 2001/0031003 A1 * | 10/2001 | Sawhney et al. | 375/240.14 |
| 2001/0035902 A1 | 11/2001 | Iddan et al. | |
| 2001/0051766 A1 | 12/2001 | Gazdzinksi | |
| 2002/0032366 A1 | 3/2002 | Iddan et al. | |
| 2002/0042562 A1 | 4/2002 | Meron et al. | |
| 2002/0080881 A1 * | 6/2002 | Honda et al. | 375/240.16 |
| 2002/0095187 A1 | 7/2002 | Thompson et al. | |
| 2002/0103417 A1 | 8/2002 | Gazdzinski | |
| 2002/0103425 A1 | 8/2002 | Mault | |
| 2002/0173718 A1 | 11/2002 | Frisch et al. | |
| 2002/0177779 A1 | 11/2002 | Adler et al. | |
| 2002/0191113 A1 | 12/2002 | Siefken | |
| 2002/0198439 A1 * | 12/2002 | Mizuno | 600/109 |
| 2003/0018280 A1 | 1/2003 | Lewkowicz et al. | |
| 2003/0020810 A1 * | 1/2003 | Takizawa et al. | 348/68 |
| 2003/0023150 A1 * | 1/2003 | Yokoi et al. | 600/300 |
| 2003/0028078 A1 | 2/2003 | Glukhovsky | |
| 2003/0040685 A1 | 2/2003 | Lewkowicz et al. | |
| 2003/0043263 A1 | 3/2003 | Glukhovsky et al. | |
| 2003/0045790 A1 | 3/2003 | Lewkowicz et al. | |
| 2003/0060734 A1 | 3/2003 | Yokoi et al. | |
| 2003/0077223 A1 | 4/2003 | Glukhovsky et al. | |
| 2003/0085994 A1 | 5/2003 | Fujita et al. | |
| 2003/0114742 A1 | 6/2003 | Lewkowicz et al. | |
| 2003/0117491 A1 | 6/2003 | Avni et al. | |
| 2003/0151661 A1 | 8/2003 | Davidson et al. | |
| 2003/0158503 A1 * | 8/2003 | Matsumoto | 600/593 |
| 2003/0167000 A1 | 9/2003 | Mullick et al. | |
| 2003/0169932 A1 * | 9/2003 | Li et al. | 382/239 |
| 2003/0181788 A1 | 9/2003 | Yokoi et al. | |
| 2003/0195415 A1 | 10/2003 | Iddan | |
| 2003/0208107 A1 | 11/2003 | Refael | |
| 2003/0213495 A1 | 11/2003 | Fujita et al. | |
| 2003/0229268 A1 | 12/2003 | Uchiyama et al. | |
| 2004/0027500 A1 | 2/2004 | Davidson et al. | |
| 2004/0073087 A1 | 4/2004 | Glukhovsky et al. | |
| 2004/0087832 A1 | 5/2004 | Glukhovsky et al. | |
| 2004/0098388 A1 * | 5/2004 | Roach et al. | 707/6 |
| 2004/0175289 A1 * | 9/2004 | Takizawa et al. | 422/20 |
| 2004/0215059 A1 * | 10/2004 | Homan et al. | 600/160 |
| 2004/0225190 A1 | 11/2004 | Kimoto et al. | |
| 2004/0242962 A1 | 12/2004 | Uchiyama et al. | |
| 2005/0015201 A1 * | 1/2005 | Fields et al. | 701/301 |
| 2005/0038321 A1 * | 2/2005 | Fujita et al. | 600/109 |
| 2005/0049461 A1 * | 3/2005 | Honda et al. | 600/160 |
| 2005/0159643 A1 | 7/2005 | Glukhovsky et al. | |
| 2005/0192476 A1 * | 9/2005 | Homan et al. | 600/118 |
| 2005/0212933 A1 * | 9/2005 | Miyanohara | 348/272 |
| 2005/0250991 A1 * | 11/2005 | Mizuno | 600/160 |
| 2005/0256372 A1 * | 11/2005 | Yokoi et al. | 600/102 |
| 2006/0233254 A1 * | 10/2006 | Lee et al. | 375/240.16 |
| 2007/0263128 A1 * | 11/2007 | Zhang | 348/700 |

FOREIGN PATENT DOCUMENTS

| | | |
|---|---|---|
| DE | 2929429 | 2/1980 |
| DE | 34 40 177 | 5/1986 |
| DE | 19723454 | 12/1998 |
| EP | 0 667 115 | 8/1995 |
| IL | 122602 | 4/2005 |
| JP | 57-45833 | 3/1982 |
| JP | 3-289779 | 12/1991 |
| JP | 4-109927 | 4/1992 |
| JP | 1992-144533 | 5/1992 |
| JP | 4-180736 | 6/1992 |
| JP | 5015515 | 1/1993 |
| JP | 10-243286 | 9/1998 |
| JP | 2001224553 | 8/2001 |
| WO | WO 92/21307 | 12/1992 |
| WO | WO 94-11040 | 5/1994 |
| WO | WO 98/11816 | 3/1998 |
| WO | WO 99/22640 | 5/1999 |
| WO | WO 99/30610 | 6/1999 |
| WO | WO 00/22975 | 4/2000 |
| WO | WO 01/08548 | 2/2001 |
| WO | WO 01/35813 | 5/2001 |
| WO | WO 01/50941 | 7/2001 |
| WO | WO 01/65995 | 9/2001 |
| WO | WO 01/87377 | 11/2001 |
| WO | WO 02/073507 | 9/2002 |
| WO | WO 02/094337 | 11/2002 |
| WO | WO 02/095351 | 11/2002 |
| WO | WO 03/010967 | 2/2003 |

| | | |
|---|---|---|
| WO | WO 03/011103 | 2/2003 |
| WO | PCT/IL03/00982 | 11/2003 |
| WO | WO 03/094723 | 11/2003 |
| WO | WO 2004/004540 | 1/2004 |
| WO | WO 2004/088448 | 10/2004 |

OTHER PUBLICATIONS

U.S. Appl. No. 10/860,028, filed Jun. 4, 2004, Iddan et al.
U.S. Appl. No. 10/493,751, filed Apr. 27, 2007, Glukhovsky et al.
U.S. Appl. No. 10/200,548, filed Jul. 23, 2003, Glukhovsky et al.
U.S. Appl. No. 10/811,013, filed Mar. 29, 2004, Iddan, Gavriel J.
U.S. Appl. No. 10/402,245, filed Mar. 31, 2003, Adler, Doron.
U.S. Appl. No. 10/860,028, filed Jun. 4, 2004, Iddan, Gavriel J. et al.
U.S. Appl. No. 10/200,548, filed Jul. 23, 2002, Glukhovsky, Arkady et al.
U.S. Appl. No. 10/493,751, filed Jul. 23, 2002, Glukhovsky, Arkady et al.
Mitchell, J. L. et al., "MPEG Video compression standard, Passage", MPEG Video Compression Standard, Chapman and Hall Digital Mulimedia Standards Series, New York, Chapman and Hall, US, 1996, pp. 21-30.
Netravali A. N. et al., "Picture Coding: A Review", Proceedings if the IEEE, New York, US, vol. 68, No. 3, Mar. 1, 1980, pp. 366-407.
Jain A.K., "Image Data Compression: A Review" Proceedings of the IEEE, IEEE, New York, US, vol. 69, No. 3, Mar. 1, 1981, pp. 349-389.
Search Report from EP 04 01 4906, mailed on Dec. 27, 2004.
U.S. Appl. No. 10/695,847, filed Oct. 30, 2003, Glukhovsky et al.
U.S. Appl. No. 10/724,109, filed Dec. 1, 2003, Glukhovsky et al.
U.S. Appl. No. 60/457,592, filed Mar. 27, 2003, Iddan.
U.S. Appl. No. 60/457,592, filed Jun. 26, 2003, Glukhovsky.
U.S. Appl. No. 60/307,605, filed Jul. 26, 2001, Glukhovsky et al.
Evaluation of the Heidelberg pH Capsule: Method of Tubeless Gastric Analysis, Yarbrough, III et al., The American Journal of Surgery, vol. 117, Feb. 1969, pp. 185-192.
Heidelberger Kapsel—ein Kleinstsender fur die pH-Messung im Magen, Lange, et al., Telefunken-Zeitung, Jg 36 (1963), Heft 5, pp. 265-270.
Manual of Photogrammery, Thompson (ed.), Third Edition, vol. Two, Copyright 1944, 1952, 1966 by the American Society of Photogrammetry.
Machine Vision: Theory, Algorithms, Practicalities—E.R. Davies, 1990.
Non-Lambertian Shading and Photometric Stereo- Tagare, et all, SPIE vol. 1260 Sensing and Reconstruction of Three-Dimensional Objects and Scenes (1990).
Robust Shape Reconstruction from combined shading and stereo information—Lee et al., SPIE vol. 1771, Applications of Digital Image Processing XV (1992), pp. 171-182.
Shedding light on cancer diagnosis—Powell (Ed.), May 2000, Laser Focus World.
Stimulation of images by photometric stereo modeling, Russel et al. Optical Engineering, Sep. 1991, vol. 30, No. 9, pp. 1337-1345.
Surface Representation from Photometric Stereo with Wavelets, Sinzinger et al. SPIE vol. 3169, 1997.
Two Image Photometric Stereo Method, Yang et al, SPIE vol. 1826, Intelligent Robots and computer vision XI (1992).
Estimating Motion in Image Sequences, Stiller et all, IEEE Signal Processing Magazine, Jul. 1999, pp. 70-91.
Robots for the future—Shin-ichi et al., Nov. 29, 2001.
Video Cameral to Take—RF System lab, Dec. 25, 2001.
www.rfnorkia.com—NORIKA3, Dec. 4, 2001.
Wang, et al., "Integrated Micro-Instrumentation for Dynamic Monitoring of the Gastro-Intestinal Tract", Presented at IEEE Instrumentation and Measurement Technology Conference, May 2002, Anchorage, Ak, USA. www.see.ed.ac.uk/Naa.publications.hotml.
Roubik, et al, Reference Microelectrodes Design Evaluation for On-Chip ISFET-Based Microsensors for "in vivo" Blood Measurements, 2000.
"Chemical Microsystems", Department of Microelectronics, Faculty of Electrical Engineering Czech Technical University in Prague, Technicka 2, CZ-166 27 Prague 6, Czech Republic, 2006, date unknown.
F. Vald's-Perezgasga, et al., "Isfet Appliations in Biological Matter: An Overview", downloaded Oct. 27, 2002, www.cinstrum.unam.mx/revista/pdfv4n3/art3.PDF.
The Radio Pill, Rowlands, et al., "British Communications and Electronics", Aug. 1960, pp. 598-601.
Wellesley company sends body monitors into space, Crum Apr. 1998.
Wireless Transmission of a color television moving image from the stomach using a miniature CCD camera light source and microwave transmitter Swain CP Gong F Mills TN Gastrointest Endosc, 1997;45:AB40.
BBC News Online—Pill Camera to broadcast from the guy—Feb. 21, 2000, www.news.bbc.co.uk.
Biomedical Telemetry, R. Stewart McKay, John Wiley and Songs, 1970, pp. 244-245.

* cited by examiner

DEVICE, METHOD, AND SYSTEM FOR REDUCED TRANSMISSION IMAGING

RELATED APPLICATION DATA

This application claims benefit from prior U.S. provisional application Ser. No. 60/482,456, filed on Jun. 26, 2003, DEVICE, METHOD, AND SYSTEM FOR REDUCED TRANSMISSION IMAGING, which is incorporated in its entirety by reference herein.

FIELD OF THE INVENTION

The invention relates to image data transmission; and in particular to a device, system and method for reduced transmission of image data.

BACKGROUND OF THE INVENTION

Devices, systems, and methods for performing in-vivo imaging of passages or cavities with a body, and for gathering information other than or in addition to image information (e.g., temperature information, pressure information), may be known in the art. Such devices may include, inter alia, various endoscopic imaging systems and devices for performing imaging in various internal body cavities.

An in-vivo imaging device may include, for example, an imaging system for obtaining images from inside a body cavity or lumen, such as, for example, the gastrointestinal (GI) tract. The imaging system may include, for example, an imager associated with an optical system, and optionally an illumination unit, a power source, a transmitter, and an antenna. Other types of in-vivo devices exist, such as, for example, endoscopes that may not require a transmitter, and, for example, in-vivo devices performing functions other than imaging.

Various operations performed by an in-vivo imaging device may consume energy provided by, for example, a power source within the device. Typically, reliable transmission of images may consume a significant amount of energy. There may be other "costs" or resource usages associated with reliably transmitting images, for example, a need to implement algorithms and/or processes for data compression, error detection and/or error correction.

SUMMARY OF THE INVENTION

Various embodiments of the invention provide an imaging device, system, and method with reduced transmission and/or reduced energy required for transmission, which may be used, for example, in an in-vivo imaging device. In some embodiments of the invention, captured images that may be substantially similar to previously transmitted images may not be transmitted, or may be only partially transmitted. In other embodiments, data other than image data may be transmitted in place of the captured image.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features and advantages thereof, may best be understood by reference to the following detailed description when read with the accompanied drawings in which:

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following description, various aspects of the invention will be described. For purposes of explanation, specific configurations and details are set forth in order to provide a thorough understanding of the invention. However, it will also be apparent to one skilled in the art that the invention may be practiced without the specific details presented herein. Furthermore, well-known features may be omitted or simplified in order not to obscure the invention.

It is noted that some embodiments of the present invention are directed to a typically swallowable in-vivo device. Other embodiments need not be swallowable. Devices according to embodiments of the present invention may be similar to embodiments described in International Application WO 01/65995 and/or in U.S. Pat. No. 5,604,531, each of which are assigned to the common assignee of the present invention and each of which are hereby fully incorporated by reference. Furthermore, a receiving and/or display system suitable for use with embodiments of the present invention may also be similar to embodiments described in WO 01/65995 and/or in U.S. Pat. No. 5,604,531. Of course, devices and systems as described herein may have other configurations and other sets of components.

Embodiments of the device may typically be autonomous and may typically be self-contained. For example, the device may be a capsule or another unit where all the components are substantially contained within a container or shell, and where the device may not require any wires or cables to, for example, receive power or transmit information. The device may, for example, communicate with an external receiving and display system to provide display of data, control, or other functions. For example, power may be provided by an internal battery or a wireless receiving system. Other embodiments may have other configurations and capabilities. For example, components may be distributed over multiple sites or units. Control information may be received from an external source.

A system and method according to various embodiments of the present invention may be used with any suitable in-vivo device. In alternate embodiments of the system and method, according to various embodiments of the invention, the system and method may be used with other suitable devices, non-imaging and/or non-in-vivo devices.

Figure 1:
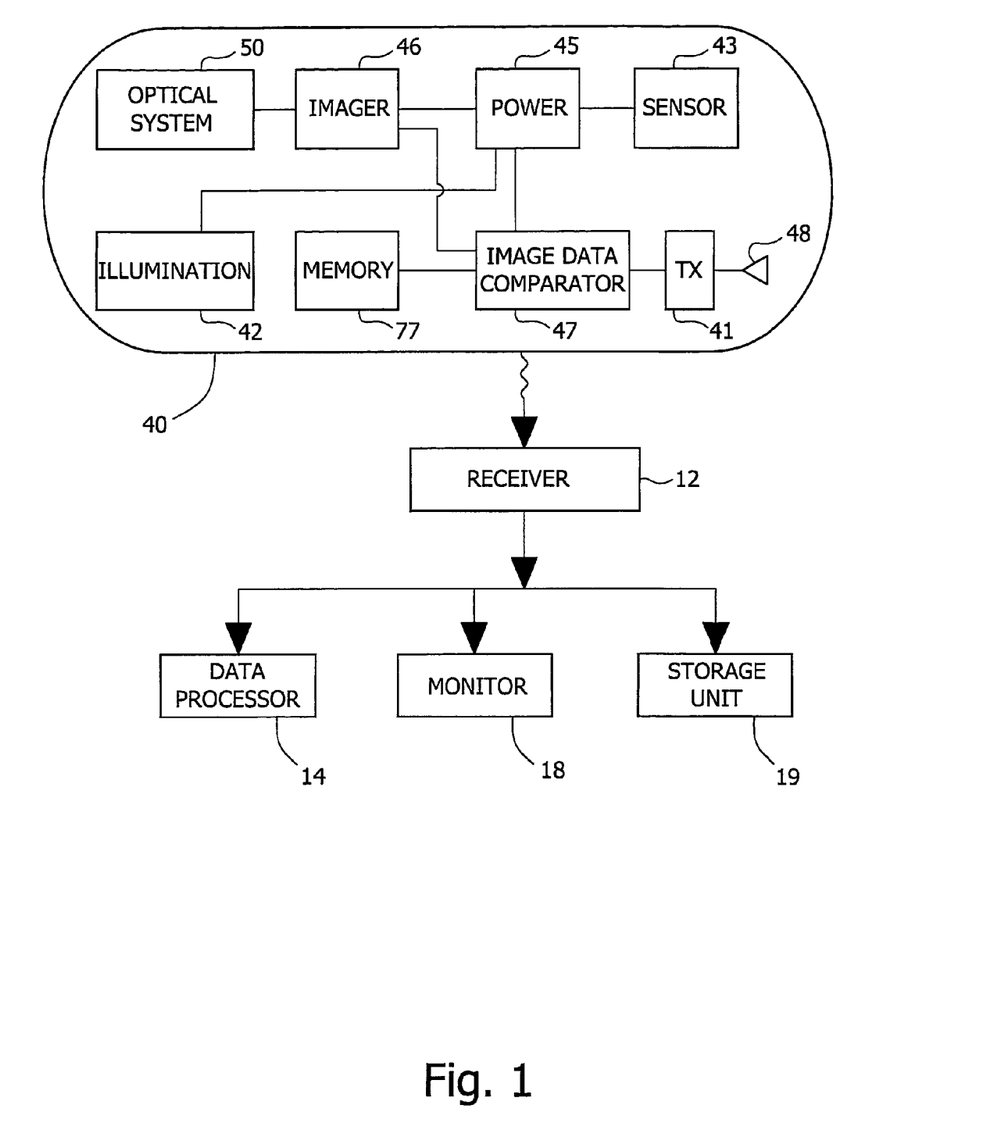
FIG. 1 is a schematic illustration of an in-vivo imaging system in accordance with embodiments of the invention.

FIG. 1 shows a schematic diagram of an in-vivo imaging system in accordance with embodiments of the present invention. In one embodiment, the system may include a device 40 having an imager 46, an illumination source 42, and a transmitter 41. In some embodiments, device 40 may be implemented using a swallowable capsule, but other sorts of devices or suitable implementations may be used. Outside the patient's body may be an image receiver 12 (including, for example, an antenna or an antenna array), a storage unit 19, a data processor 14, and a display unit or monitor 18. While FIG. 1 shows separate monitors, in some embodiments, both an image and its position may be presented using a single monitor. Other suitable systems and methods of storing and/or displaying collected image data may be used.

In some embodiments, device 40 may include a memory and/or storage unit 77, to store data, for example, image data captured using imager 46. In one embodiment, storage unit 77 may, for example, have storage capacity sufficient to store data representing one image or a plurality of images captured using imager 46. In an alternate embodiment, storage unit 77 may, for example, have storage capacity sufficient to store parameters related to image data of one or more images, for example, histogram parameters or Fast Fourier Transform (FFT) parameters and/or coefficients of one or more images, or other parameters or data; in some embodiments, such storage capacity may, for example, be lower or significantly lower than the storage capacity that may be required to store an image or a plurality of images.

Transmitter 41 may typically operate using radio waves, but in some embodiments, such as those where the device 40 may be or may be included within an endoscope, transmitter 41 may transmit via, for example, wire, optical fiber and/or other suitable methods.

Device 40 typically may be or may include an autonomous swallowable capsule, but may have other shapes, and need not be swallowable or autonomous. In one embodiment, device 40 includes an in-vivo camera, including for example, an imager 46, that may, for example, capture and transmit images of the GI tract as the capsule passes through the GI lumen. Typically, device 40 may capture a stream of images. In some embodiment of the invention, images captured may, for example, be useful in revealing pathological conditions of the GI tract. Other lumens may be imaged.

In one embodiment, imager 46 in device 40 may, for example, be in electrical communication with transmitter 41. Transmitter 41 may, for example, transmit image data to image receiver 12. Image data may subsequently be stored, processed, displayed, etc. with, for example, data processor 14, to storage unit 19, and display unit or monitor 18. Transmitter 41 may, for example, also include control capability, although control capability may be included in a separate component. Transmitter 41 may include any suitable transmitter able to transmit images and/or other data (e.g., control and/or telemetry data) to a receiving device. For example, transmitter 41 may include an ultra low power Radio Frequency (RF) high bandwidth transmitter, possibly provided in Chip Scale Package (CSP). Transmitter 41 may, for example, transmit via antenna 48.

Additionally, transmitter 41 and/or device 40 may include a control unit that may include circuitry and/or functionality for controlling device 40.

Transmitter 41 may, for example, contain or process instructions. In some embodiments the instructions embodying an error correction code may be included in an encoder that may be part of or connected to transmitter 41. In alternate embodiments such functionality may, for example, be placed in an alternate units, for example, be placed in a processing unit.

Typically, device 40 may include an image data comparator unit 47, for example, to compare image data captured by imager 46 and/or stored in memory 77. Image comparison may be, for example, by processing signals and/or data generated by imager 46. In some embodiments, image comparator unit 47 need not be a separate component; for example, image data comparator unit 47 or its functionality may be integral to imager 46, or to transmitter 41, or other suitable component. In some embodiments, image comparator unit 47 may perform comparison operations, for example, comparison between images in an image stream, analysis operations and/or decision operations as described herein.

Power source 45 may include, for example, one or more batteries. For example, power source 45 may include silver oxide batteries, lithium batteries, other suitable electrochemical cells having a high energy density, or the like. Other power sources may be used. For example, instead of internal power source 45 or in addition to it, an external power source (e.g., a power transmitter) may be used to transmit power to device 40.

Data processor 14 may, for example, analyze the data received from device 40, and may be in communication with storage unit 19, transferring image data to and from storage unit 19. Data processor 14 may also provide the analyzed data to monitor 18, where a user may view the data. Monitor 18 may present an image of the GI lumen, as well as the position in the GI tract (or other body lumen or cavity imaged) at which the image was taken. In one embodiment, data processor 14 may be configured for real time processing and/or for post processing to be performed and/or viewed at a later time.

In some embodiments, in addition to revealing pathological conditions of the GI tract, the system may provide information about the location of these pathologies. Suitable location detection systems, and/or tracking devices and methods of determining location are described in embodiments of the above-mentioned U.S. Pat. No. 5,604,531 and/or U.S. Patent Application Publication No. US-2002-0173718-A1, filed May 20, 2002, titled "Array System and Method for Locating an In-Vivo Signal Source", assigned to the assignee of the present invention, and fully incorporated herein by reference.

It is noted that in embodiments of the invention, other location and/or orientation detection methods may be used. In one embodiment, the orientation information may include three Euler angles or quaternion parameters; other orientation information may be used. In one embodiment, location and/or orientation information may be determined by, for example, including one or more transmitting antennas in device 40, to transmit data using various frequencies, and/or by detecting the location and/or orientation of device 40 using magnetic means, for example, components of quasi-static magnetic field(s). In some embodiments, methods such as those using ultrasound transceivers or monitors that include, for example, three magnetic coils that may receive and transmit positional signals relative to an external constant magnetic field may be used. For example, device 40 may include an optional tracking and/or movement sensor 43.

In one embodiment, a Global Positioning System (GPS)-like system may be used; for example, a system using transmission from three or more stations. In one embodiment, if a phase and a frequency are used which are sufficiently high frequency (e.g., 300 Megahertz), a resolution of 1 millimeter is possible. Other suitable GPS like systems may be used in accordance with embodiments of the invention. For example, an array of antennas or sensors may be placed on or close to the abdomen to enable tracking of device 40. Of course, other suitable components or sets of components may be used in accordance with embodiments of the invention.

In some embodiments, device 40 may include one or more illumination sources 42, for example one or more white LEDs or any other suitable light source, for illuminating the body lumen. An optical system 50, including, for example, one or more optical elements, such as one or more lenses or composite lens assemblies, one or more suitable optical filters, or any other suitable optical elements, may aid in focusing reflected light onto imager 46 and performing other light processing.

Typically, device 40 may transmit image information, for example, in discrete portions. Each portion may typically correspond to an image or frame. Other transmission methods are possible. For example, device 40 may capture an image, for example, once every half second, and, after capturing such an image and possibly after a suitable decision or analysis (for example, a decision to transmit or not to transmit, or to transmit partial information), may transmit the data to receiver 12. Other constant and/or variable capture rates and/or transmission rates may be used and, as discussed herein, certain images need not be transmitted.

Typically, the image data recorded and transmitted may be digital color image data, although in alternate embodiments other image formats (e.g., black and white image data) may be used. In one embodiment, each frame of image data includes 256 rows of 256 pixels each, each pixel including data for color and brightness, according to known methods. For example, in each pixel, color may be represented by a mosaic of four sub-pixels, each sub-pixel corresponding to primaries such as red, green, or blue (where one primary is represented twice). The brightness of the overall pixel may be recorded by, for example, a one byte (e.g., 0-255) brightness value. Other data formats may be used.

Embodiments of the invention may increase efficiency of energy consumption, for example, by transmitting images at a variable rate, and/or by transmitting data using a variable format. In some embodiments, transmission of images and/or data may be performed at a variable rate that may be, substantially and/or on average, lower than a comparable fixed rate. It is noted that while some exemplary embodiments are explained in detail herein, the invention is not limited in this regard, and other embodiments and/or implementations of such energy-efficient imaging devices or devices having other or different benefits are also within the scope of the invention. Further, different and/or other benefits may be achieved in accordance with various embodiments of the invention.

In one embodiment, after image data may be captured by imager 46 but before the image is transmitted by transmitter 41, a determination may be made as to whether the currently captured image is substantially similar and/or identical to a previously transmitted image. Such a determination may be made, for example, by image comparator 47, which may be implemented as an integrated part of transmitter 41, or of imager 46, or as a separate unit within device 40. Image comparator 47 may be implemented in any suitable manner, such as part of the circuitry of transmitter 41. In one embodiment of the invention, if the currently captured image is substantially similar and/or identical to another image, for example, a previously transmitted image, then the currently captured image may not be transmitted; otherwise, the currently captured image may be transmitted. In some embodiments, the previously transmitted image may be the most recently transmitted image, may be another image, or may be, for example, a set of image data used for comparison and/or analysis. Typically, image data or data extracted or computed from a previously transmitted image may be temporarily stored in memory 77. In other embodiments of the invention, image data, other than previously transmitted image data may be stored in memory 77 for comparison to captured image data. Furthermore, in alternate embodiments, data other than image data may be transmitted or not transmitted based on an algorithm(s) containing comparison and/or an analysis.

Figure 2:
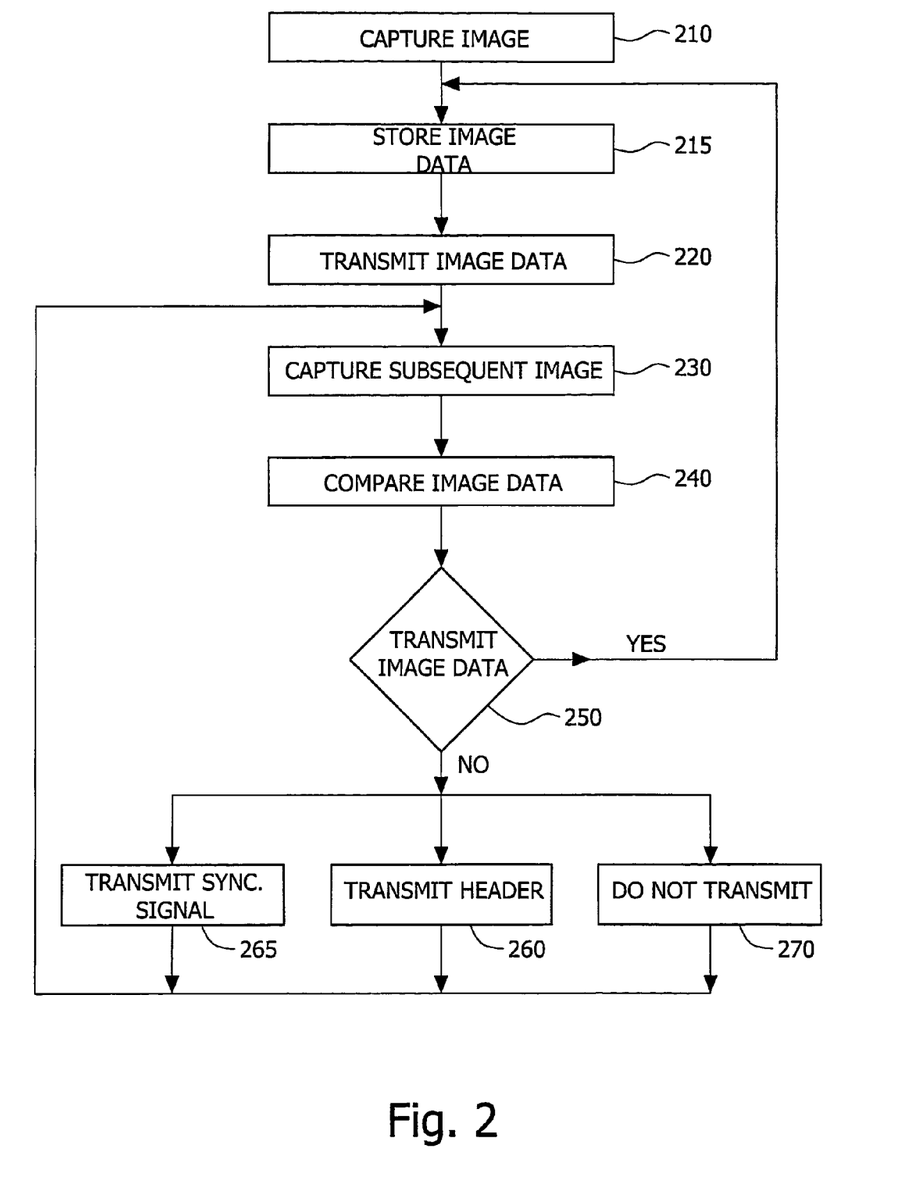
FIG. 2 is a flow chart diagram of a method of transmitting image data and/or other data at a variable rate in accordance with embodiments of the invention.

FIG. 2 is a flow chart diagram of a method of transmitting images and/or data in accordance with embodiments of the present invention. As indicated at block 210, an image may be captured, for example, by imager 46. As indicated at block 215 image data from image may be stored in, for example, memory unit 77. As indicated at block 220, the image may be transmitted, for example, by transmitter 41. As indicated at block 230, a subsequent image may be captured, for example, by imager 46.

In embodiments of the invention, as indicated at block 240, an analysis may be performed to determine whether it may be required and/or desired to transmit the subsequent image. Any suitable criteria may be used for such a check and/or determination. For example, in one embodiment, the subsequent image data may be stored in memory 77 as well as transmitted if the subsequent image differs more than defined threshold as compared to a previously transmitted image (difference between the images may be determined by number of different methods described herein). Other suitable criteria or methods for analysis may be used in accordance with embodiments of the invention. Some exemplary methods for the analysis are detailed herein and with reference to FIG. 3.

It is noted that in some embodiments, the analysis and/or comparison may be performed, for example, using image data comparator 47 and/or using an alternate dedicated comparator unit, and using any suitable combination of hardware and/or software. The analysis and/or comparison may, for example, take into account, for example, various changes between images related to size, dimensions, light, color, brightness, contrast, borders, margins, focus, horizontal and/or vertical shifting, etc. For example, in one embodiment, the analysis may determine that a subsequent image may be substantially similar and/or identical to a previously transmitted image possibly except, for example, that one of the images may be larger and/or brighter than the other, and may conclude that the subsequent image may not be transmitted.

As indicated at block 250, if it was determined that it is required and/or desired to transmit the subsequent image, then the subsequent image may be, for example, stored in memory 77 and transmitted, for example, using transmitter 41. In some embodiments, as indicated, optionally, instead of transmitting the captured image of the subsequent image, data representing differences between the subsequent image and the recently transmitted image may be transmitted; this may be performed, for example, utilizing a suitable Moving Picture Experts Group (MPEG) codec and/or algorithm to detect and/or represent differences between images. It is noted that transmitting data representing differences between images may be used in various embodiments of the invention, for example, an embodiment utilizing a fixed transmission rate, a fixed transmission format, and/or a fixed transmission/reception system.

Alternatively, as indicated at decision block 250, if it was determined that it is not required and/or undesired to transmit the subsequent image, then, optionally, as indicated at block 260, a header may be transmitted; or, in some embodiments, optionally, as indicated at block 265, a synchronization signal may be transmitted; or, in some embodiments, optionally, as indicated at block 270, no data may be transmitted and transmission may be skipped. In other embodiments of the present invention, a header, synchronization signal, or other suitable data or signals may be transmitted along with image data.

In some embodiments, a header may include less data, or significantly less data, than an image. In one embodiment, the header may include data that may, for example, indicate the transmission time of the header. In other embodiments of the invention, the header may include, for example, an identifier and/or descriptor for the imaging device. In yet other embodiments of the invention, the header may include telemetry data, for example, data indicating the position and/or location of device 40 within the body. In alternate embodiments of the invention, the header may include, for example, pH data, temperature data, pressure data, electrical parameters and/or data, acceleration data, data indicating status of power source 45, localization parameters, illumination parameters and/or data, and/or other suitable or desired data. The header may include data to indicate the serial number or sequence number of the non-transmitted image within an image stream. The header may include synchronization data and/or sequence data, a series number and/or a serial number; such synchronization signal and/or data may be used, for example, by receiver 12 to keep synchronization with device 40 and/or to indicate to receiver 12 that device 40 and/or power source 45 are operational. For exemplary purposes only, in one embodiment, a header may include, for example, data reflecting and/or encapsulating the following information: "Image number 753 is not transmitted, by device number 957, at local time 11:53:42, at position (14, 39, 26) within the GI tract". Of course, a header may include other contents and information, and other data formats may be used.

In some embodiments, image data that may be transmitted may also be temporarily stored for future reference, for example, for subsequent analysis and/or for comparison to a subsequent image. Such image data may be stored, for example, in storage unit 77 within device 40. In some embodiments of the invention, image data may refer to, for example, an image frame, more than one image frame, part of an image frame, and/or parameters derived from an image frame or from more than one image frame. For example, if image data from a first image may be temporarily stored in memory 77 as well as transmitted, and image data from a second image may be analyzed with image comparator 47, temporarily stored in memory 77, and transmitted, and a third image may be captured, then image data from the third image may be analyzed and/or compared against the image data from the second image, and not against the first image. In some embodiments of the present invention, image data stored in memory 77 may be discarded and/or replaced by subsequent image data captured or otherwise obtained. In other embodiments of the present invention, image data from an image may be analyzed and/or compared against more than one image. In some embodiments, any suitable combination of comparing two or more images may be used.

Additionally or alternatively, in some embodiments, a subsequent image may be transmitted if a pre-defined criterion is met, even if the analysis and/or comparison determined that it is not required to transmit the subsequent image. In one embodiment, a subsequent image may be transmitted if a pre-defined number of headers, or consecutive headers, were transmitted, or if a pre-defined number of prior images were skipped and not transmitted. For example, in one embodiment, a subsequent image may be transmitted if it follows, for example, 10 consecutive transmissions of headers instead of images, or, for example, 13 non-transmitted images, etc. Of course, other threshold values and/or criteria may be used in accordance with embodiments of the invention. Additionally or alternatively, in one embodiment, for example, a subsequent image may be transmitted if a pre-defined period of time elapsed since the most recent transmission of an image. For example, in one embodiment, a subsequent image may be transmitted if, for example, 6 seconds elapsed since the most recent image transmission. Of course, other threshold values and/or criteria may be used in accordance with embodiments of the invention.

Additionally or alternatively, in one embodiment, for example, a subsequent image may be skipped and not transmitted if it may be detected that device 40 may not be not in motion and/or may not be accelerating, for example, using a movement sensor, using an accelerometer unit, by measuring external impedance, etc.; this may occur, for example, if device 40 is located inside the colon for a relatively long period of time. In some embodiments, a subsequent image may be transmitted even if no motion and/or no acceleration are detected, for example, if a pre-defined time interval elapsed since the most recent transmission of an image.

It is noted that in some embodiments, the image data transmitted as indicated in block 250 may be compressed. Additionally or alternatively, in some embodiments, the header data transmitted as indicated in block 260, or other data transmitted (for example, synchronization signal data, or data representing differences between images) may be compressed. Such compression or compressions may allow, for example, saving transmission energy and/or transmission time and/or memory space and/or data storage space.

In some embodiments, as indicated in the flow chart diagram of FIG. 2, the operations described above may be repeated and/or applied to consecutive images. For example, a third image may be captured, and an analysis may be performed to determine whether to transmit the third image. In one embodiment, the analysis may include, for example, a comparison of the third image with the second image, or an analysis of the third image with the most recently transmitted image. In one embodiment, an image may be transmitted every half second, unless it may be substantially similar to a previously transmitted image. Of course, other suitable methods for analysis may be used, for example, one or more of the exemplary methods for analysis detailed herein, for example, with reference to FIG. 3. It is noted that in some embodiments, if a header may be sent instead of image data, and an additional image may be captured, then the additional image may be compared, for example, to the most recently transmitted image, and not to the most recently captured image. In some embodiments, any suitable combination of comparing two images may be used.

In some embodiments, display unit 18 may automatically adjust to and/or operate in accordance with the transmissions received. In one embodiment, if image data, for example, is not transmitted, image monitor 18 may continue to display the most recently displayed data or image, or may "freeze" current display. In an alternate embodiment, image monitor 18 may "fill in" a gap which may result when an image is not transmitted, for example, by adjusting the time period for displaying each image, by using a variable refresh rate of the display units, by using a suitable morphing technique and/or a suitable transformation algorithm to smoothly morph a first image into a non-subsequent image, etc. It is noted that in one embodiment, such operations and/or adjustments in operations of image display unit 18 may be calculated, processed and/or performed, for example, using data processor 14 or other suitable processors. In another embodiment, if partial data is transmitted, image display unit 18 or data processor may use the partial data to create new images to display as part of the display stream, using known image reconstruction techniques (e.g., MPEG techniques).

Figure 3:
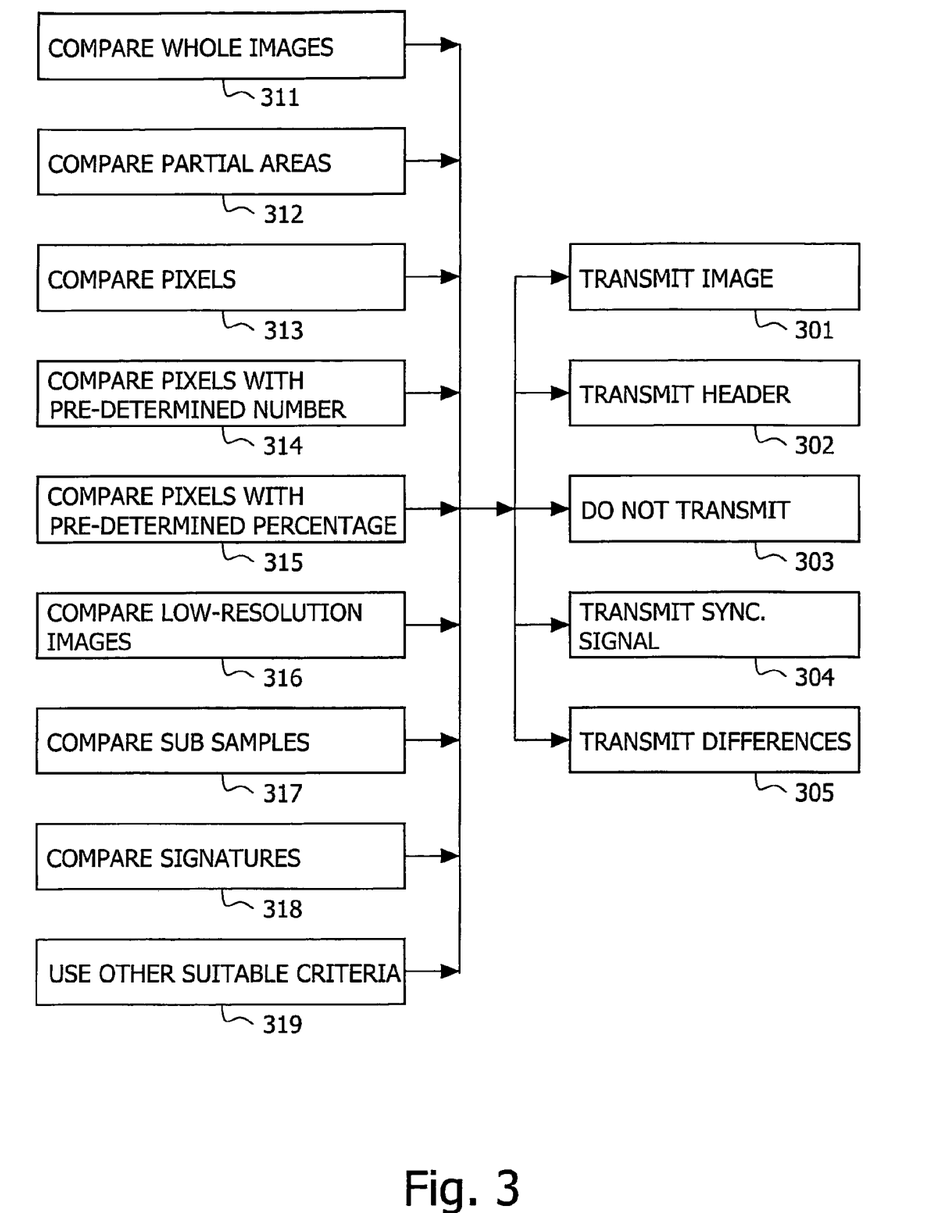
FIG. 3 is a flow chart diagram of a method of analysis to determine whether to transmit an image in accordance with embodiments of the invention.

FIG. 3 is a flow chart diagram of a method of analysis to determine whether to transmit an image or part of an image in accordance with embodiments of the invention. In some embodiments, one or more of the operations or analyses indicated in blocks 311-319 may be used, for example, to determine whether to transmit a second image after a first image had been captured. Each of blocks 311-319 represent an analysis that may be performed in an embodiment of the invention; in some embodiments, more than one method of analysis or decision may be used. In some embodiments, the determination may result, for example, in transmitting image data (block 301), transmitting a header (block 302), transmitting a synchronization signal (block 304), transmitting data representing differences between images (block 305), or not transmitting (block 303). Suitable analyses other than those listed may be used in accordance with embodiments of the invention.

It is noted that for purposes of simplification only, the discussion herein refers to a first image and to a second image. Of course, the method of FIG. 3 may be applied to any other image or images, including, for example, repeatedly to a series of consecutive and/or non-consecutive images. For example, more than two images may be compared to determine weather or not to transmit one or more images.

In one embodiment, as indicated in block 311, an analysis may be performed such that the second image may be transmitted if the second image may be, for example, different, or generally different, or substantially different, than the first image.

In one embodiment, as indicated in block 312, an analysis may be performed such that, for example, the second image may be transmitted if one or more partial areas and/or locations within the second image may be different, or generally different, or substantially different, than one or more corresponding partial areas and/or locations within the first image.

In one embodiment, as indicated in block 313, an analysis may be performed such that, for example, the second image may be transmitted if a pixel or a plurality of pixels within the second image may have different, or substantially different, or generally different properties than a corresponding pixel or a corresponding plurality of pixels within the first image. In some embodiments, such properties may include, for example, color properties, Red-Green-Blue (RGB) properties, Hue-Saturation-Value (HSV) properties, Cyan-Magenta-Yellow (CMY) properties, Cyan-Magenta-Yellow-black (CMYK) properties, or any other suitable pixel property or properties. In some embodiments, a plurality of pixels may be analyzed and/or compared; for example, a plurality of pixels within a pre-defined area or shape may be analyzed, or a plurality of pixels defined in real-time using a formula or an equation may be analyzed, etc. It is noted that in some embodiments, the plurality of pixels analyzed need not be of a pre-defined number; for example, an analysis may be performed on a plurality of pixels that may have a certain property, e.g., pixels with a substantially red color, or other suitable properties. Images' transformations may be compared rather than the images themselves (e.g. histograms, FFT transforms, etc.). In alternate embodiments, known algorithms may be implemented, for example, fuzzy algorithms, neural networks, etc.

In one embodiment, as indicated in block 314, an analysis may be performed such that a second image may be transmitted if a pre-determined number of pixels in the second image may be different, or substantially different, or generally different, than the corresponding pixels in a first image.

In one embodiment, as indicated in block 315, an analysis may be performed such that, for example, the second image may be transmitted if a pre-determined percentage of pixels in the second image may be different, or substantially different, or generally different, than the corresponding pixels in the first image. Such analysis may be used, for example, in some embodiments using images that have various sizes and/or resolutions.

In one embodiment, as indicated in block 316, an analysis may be performed such that, for example, a low-resolution version of the second image may be compared to a corresponding low-resolution version of the first image. In some embodiments, for example, the low-resolution version may be captured by imager 46 and/or device 40, and/or may be processed and/or prepared by image comparator 47 and/or other components in device 40.

In one embodiment, as indicated in block 317, an analysis may be performed such that, for example, a sub-sample of the second image may be compared to a corresponding sub-sample of the first image. A sub-sample of an image may include, for example, one or more lines (e.g., seven lines) of an image. In some embodiments, a sub-sample may be selected based upon a desired and/or pre-defined criterion, for example, based upon illumination parameters and/or illumination conditions. In some embodiments, comparing and/or analyzing sub-samples of images may include, for example, comparing and/or analyzing each second, third, fourth or Nth pixel, or another sub-set of pixels; such pixels may be, for example, spread evenly or unevenly across the images, for example, such that the sub-sample may include more pixels in the central region of the image and less pixels in the margin regions and/or corner regions and/or less-illuminated regions of the image.

In one embodiment, as indicated in block 318, an analysis may be performed such that a data signature of a second image may be compared to a data signature of a first image. Such data signatures may be based, for example, on any suitable criteria and/or formulae, such as a suitable data hashing formula or a suitable Cyclic Redundancy Check (CRC) algorithm. Of course, other suitable criteria, formulae and/or data signatures may be used in accordance with embodiments of the invention.

In one embodiment, as indicated in block 319, an analysis may be performed such that, for example, any other suitable criteria and/or mechanism may be used to determine whether to transmit an image. In one embodiment, Fast Fourier Transform (FFT) parameters and/or coefficients may be calculated and compared and/or analyzed. Histograms and/or color histograms may be extracted, calculated, compared and/or analyzed. Additionally or alternatively, in one embodiment, an ultrasonic sensor and/or motion detector may, for example, determine whether imager 46 and/or device 40 are in motion, as a criterion for transmitting images. An accelerometer or other suitable device may be used to determine whether imager 46 and/or device 40 are in motion and/or accelerating and/or decelerating, as a criterion for transmitting images. Other known image comparison methods may be used.

In one embodiment, the comparison and/or analysis operations may be based upon, or may be performed in accordance with, a suitable illumination control method, for example, a method or an algorithm to determine and/or control the amount, timing, intensity or other properties of illumination for capturing images. In one embodiment, such method or algorithm may be in accordance with one or more suitable embodiments as described in United States Patent Publication number US20030117491, entitled "Apparatus and Method for Controlling Illumination in an In-Vivo Imaging Device" and published on Jul. 26, 2003, which is assigned to the common assignee of the present invention, and which is fully incorporated herein by reference. For example, in one embodiment, since analysis of identical and/or similar images may yield identical and/or similar illumination control parameters, it may be determined that images with substantially identical and/or similar illumination control parameters may be substantially similar to each other, for purposes of image comparison and/or image analysis. In one embodiment, control pixels and parameters may be used within an initial and/or fast process, to calculate and/or determine properties of required or desired illumination; values of such control pixels and parameters, that may be calculated separately for each image, may be analyzed or compared to determine similarity or difference between images. For example, identifying two images having different values of control pixels or illumination parameters, may lead to a determination that the two images may not be substantially similar, or that it may be desired or required to transmit both images. Other suitable parameters and values used within an illumination process may be used for purposes of analysis and/or comparison in accordance with embodiments of the invention.

It is noted that typically, a recently captured image may be compared to the most recently transmitted image, to determine whether to transmit the recently captured image. However, other suitable criteria may be used in accordance with embodiments of the invention. Further other images may be compared—for example one or more images may be compared In some embodiments, analysis of images may include, for example, any suitable operations to facilitate the analysis and/or comparisons. For example, in some embodiments, such pre-processing operations may be performed to, for example, remove borders and margins, modify image attributes and/or properties, modify pixel attributes and/or properties, resize images, center or move images, rotate images, flip images horizontally and/or vertically, mirror images, perform zoom-in, perform zoom-out, modify brightness and/or color levels, etc.

In one embodiment, a variable transmission rate may, for example, be combined, if desired and/or if suitable to achieve various functionalities, with a fixed and/or a variable capture rate of image by imager 46, and/or with a fixed and/or a variable display rate of images by image monitor 18.

It is noted that in some embodiments, a plurality of checks and/or comparisons may be combined to reach a determination whether to transmit the second image. In some embodiments, such checks and/or comparisons may be performed, for example, consecutively and/or in parallel.

In some embodiments, the checks as indicated at block 230 and/or the comparisons described herein may be performed, for example, using image comparator 47. However, in some embodiments, a processing unit and/or circuitry may be used to perform such checks, analyses and/or comparisons. Furthermore, in some embodiments, suitable memory units and/or storage areas and/or buffers may be used to facilitate the operations described herein and/or to store image data for short terms and/or long terms. Additionally or alternatively, in some embodiments, the checks and/or comparisons described herein may be performed using any suitable combination of hardware and/or software.

In some embodiments, it may be, for example, more advantageous to perform reduced transmissions when the quality of the communications involved may be relatively high. For example, in an embodiment using high-quality communications, in which the Bit Error Rate (BER) is low, reduced transmissions may be relatively more beneficial in comparison to a low-quality, high-BER communications channel. In one embodiment, reduced transmissions may be performed if a pre-defined criterion may be met, for example, if the quality of the communication channel may be above a pre-defined threshold value, if the BER of the communication channel may be below a pre-defined threshold value, or if other suitable criterion is met. In other embodiments, when, for example, using poor communication channels, it may be more advantageous to transmit fewer images but to increase the transmission power. In some embodiments, reduced transmission may be turned on or turned off according to these criteria or other suitable criteria.

It is noted that in some embodiments, device 40 may include a plurality of imagers similar to imager 46, for example, to capture a broad field-of-view. In such embodiments, it may be more advantageous to perform reduction of transmissions separately for the images captured by each imager.

Figure 4:
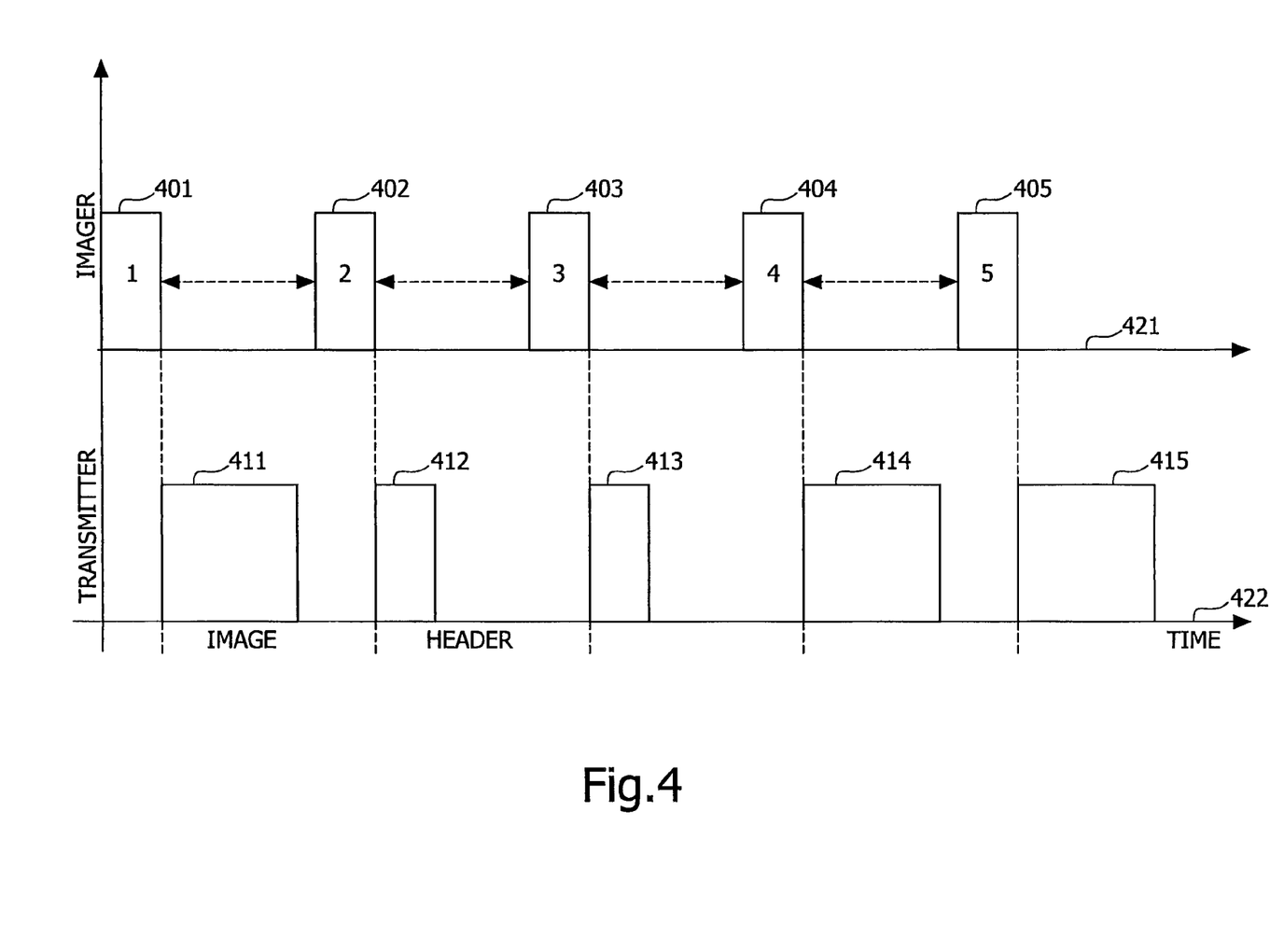
FIG. 4 is a schematic illustration of a graph indicating time periods of operation of an imager and a transmitter in accordance with embodiments of the invention.

FIG. 4 shows a schematic illustration of a graph indicating time periods of operation of imager 46 and transmitter 41 in accordance with some embodiments of the invention. It is noted that FIG. 4 is provided for exemplary purposes only, and that other graphs of operation may result from using various embodiments of the invention and/or in other operation scenarios.

Axis 421 indicates a timeline for operations of imager 46, while axis 422 indicates a timeline for operations of transmitter 41. In some embodiments, both timelines may, for example, overlap and/or be identical. Imager 46 may capture images, for example, at a constant rate, but a system and method of the present invention may be used with systems transmitting at variable rates. Such images may be captured, for example, during time periods 401, 402, 403, 404, and 405. Further, other components within a device according to an embodiment of the present invention may perform the functions depicted in FIG. 4.

After an image may be captured, transmitter 41 may transmit image data, or header data, or a synchronization signal, or data representing differences between images, other suitable data, or in some embodiments, no data. For example, in time periods 411, 414 and 415, transmitter 41 may transmit image data, and in time periods 412 and 413, transmitter 41 may transmit header data.

In one example illustrated in FIG. 4, a first image may be captured, for example, using imager 46, and its image data may be transmitted, for example, using transmitter 41, in time period 411.

A second image may be captured, for example, using imager 46, in time period 402. As described above, an analysis may be performed to determine whether it is required and/or desired to transmit the second image. In one embodiment, such analysis may include, for example, a comparison of the second image to the first image. In the example of FIG. 4, the result of the analysis may be, for example, that the second image may not be substantially different from the first image, and/or that it is not required and/or desired to transmit the second image. Hence, header data may be transmitted, for example, using transmitter 41, in time period 412.

A third image may be captured, for example, using imager 46, in time period 403. As described above, an analysis may be performed to determine whether it is required and/or desired to transmit the third image. In one embodiment, such analysis may include, for example, a comparison of the third image to the first image. It is noted that since, in the example of FIG. 4, the second image was not transmitted, it may be desired to compare the third image to the first image and not to the second image. In the example of FIG. 4, the result of the analysis may be, for example, that the third image is not substantially different from the first image, and/or that it is not required and/or desired to transmit the third image. Hence, header data may be transmitted, for example, using transmitter 41, in time period 413.

A fourth image may be captured, for example, using imager 46, in time period 404. As described above, an analysis may be performed to determine whether it is required and/or desired to transmit the fourth image. In one embodiment, such analysis may include, for example, a comparison of the fourth image to the first image. It is noted that since, in the example of FIG. 4, the second image and the third image were not transmitted, it may be desired to compare the fourth image to the first image and not to the second image or to the third image. In the example of FIG. 4, the result of the analysis may be, for example, that the fourth image may be significantly different from the first image, and/or that it may be required and/or desired to transmit the fourth image. Hence, image data of the fourth image may be transmitted, for example, using transmitter 41, in time period 414.

A fifth image may be captured, for example, using imager 46, in time period 405. As described above, an analysis may be performed to determine whether it is required and/or desired to transmit the fifth image. In one embodiment, such analysis may include, for example, a comparison of the fifth image to the fourth image. It is noted that since, in the example of FIG. 4, the fourth image was transmitted, it may be desired to compare the fifth image to the fourth image. In the example of FIG. 4, the result of the analysis may be, for example, that the fifth image may be substantially different from the fourth image, and/or that it may be required and/or desired to transmit the fifth image. Hence, image data of the fifth image may be transmitted, for example, using transmitter 41, in time period 415.

As illustrated in FIG. 4, in some embodiments of the invention, the time period required for transmitting header data may be shorter, or significantly shorter, than the time period required for transmitting image data. Additionally or alternatively, in some embodiments, the amount of energy required for transmitting header data may be smaller, or significantly smaller, than the amount of energy required for transmitting image data.

It is noted that embodiments of the invention may be used, for example, in conjunction with constant and/or variable capture rate, constant and/or variable transmitting rate, constant and/or variable receiving rate, constant and/or variable processing rate, constant and/or variable storing rate, and/or constant and/or variable format of transmission content. Of course, any suitable formats and/or rates may be used in accordance with embodiments of the invention.

It will be appreciated that some embodiments of the invention may achieve and/or increase efficiency in energy consumption, for example, by determining whether to transmit an image, by transmitting reduced image data and/or by transmitting header data.

However, the present invention is not limited in this regard. Embodiments of the invention may achieve and/or allow various other benefits, for example, reduction in transmitting time, reduction in receiving time, reduction in processing time, or reduction in storage space. Furthermore, using embodiments of the invention to transmit image data and/or header data may, for example, reduce and/or eliminate a need to synchronize between transmitter 41 and receiver 12, or reduce and/or eliminate various other errors associated with synchronization and/or timing.

In one embodiment, transmitter 41 may be, for example, the most energy-consuming component within device 40; for example, transmitter 41 may consume and/or require more energy, or significantly more energy, than imager 46, illumination source 42 or comparator 47. In one embodiment, such power consumption by transmitter 41 may result, for example, from the attenuation of transmitted signals by body tissues. Therefore, some embodiments of the invention may be beneficial in saving energy by reduction in transmitted data and/or transmission time, while other components within device 40 may continue to function continuously and without interruption.

While certain features of the invention have been illustrated and described herein, many modifications, substitutions, changes, and equivalents may occur to those of ordinary skill in the art. It is, therefore, to be understood that the appended claims are intended to cover all such modifications and changes as fall within the true spirit of the invention.

The invention claimed is:

1. A method for reduced transmission of an image stream captured in-vivo, the method comprising:
  performing processing in an autonomous in-vivo imaging device, the processing comprising:
    determining similarity between captured image data and image data previously transmitted in a communication channel, by comparing sub-samples of image pixels from the captured image data and the image data previously transmitted;
    determining a quality level of the communication channel; and
    if the captured image data is substantially similar to the image data previously transmitted, and if the quality level of the communication channel is above a predefined threshold value, reducing transmission of the captured image data.

2. The method according to claim 1 wherein the determining similarity is by comparing a HSV property of the captured image data and the image data previously transmitted.

3. The method according to claim 1 wherein the determining similarity is by comparing a FFT transform of at least a sub-sample of the captured image data and the image data previously transmitted.

4. The method according to claim 1 wherein the determining similarity is by comparing a data signature of the captured image data and the image data previously transmitted, wherein said data signature includes a data hashing formula or a Cyclic Redundancy Check.

5. The method according to claim 1 wherein the determining similarity is by determining if a difference between the captured image data and the image data previously transmitted is above a threshold.

6. The method according to claim 1 wherein the reducing transmission is by skipping transmission of the captured image data.

7. The method according to claim 1 wherein the reducing transmission is by transmitting a difference between the captured image data and the image data previously transmitted.

8. The method according to claim 1 wherein the reducing transmission is by transmitting a header and by skipping the transmission of data, wherein said data is the captured image data, or a difference between the captured image data and the image data previously transmitted.

9. The method according to claim 8 wherein the header comprises a time of transmission.

10. The method according to claim 1 comprising transmitting a synchronization signal, wherein said signal is to synchronize between a transmitter and a receiver.

11. The method according to claim 1 wherein the image data previously transmitted is temporarily stored in the in-vivo imaging device.

12. The method according to claim 1 comprising:
capturing image data of a body lumen; and
storing the image data.

13. The method according to claim 1 wherein determining a quality level of the communication channel comprises determining a Bit Error Rate of the communication channel.

14. An in-vivo device for transmitting image data, the device comprising:
   an imager;
   an illumination source;
   an image data comparator, configured to determine similarity between captured image data and image data previously transmitted in a communication channel;
   a memory unit;
   a transmitter to transmit image data, said transmitter configured to perform reduced transmissions of the image data if the captured image data is substantially similar to the image data previously transmitted in a communication channel, and if a quality level of the communication channel is above a pre-defined threshold value; and
   wherein the in-vivo device is an autonomous in-vivo device.

15. The in-vivo device according to claim 14 wherein the imager is a CMOS imager.

16. The in-vivo device according to claim 14 wherein the image data comparator is to compare whole images.

17. The in-vivo device according to claim 14 wherein the image data comparator is to compare FFT coefficients of image data.

18. The in-vivo device according to claim 14 wherein the memory is to store one line of image data.

19. The in-vivo device according to claim 14 wherein the memory is to store a plurality of images.

20. The in-vivo device according to claim 14 wherein the memory is to store image parameters.

21. The in-vivo device according to claim 14 wherein the image data comparator is integral to the transmitter.

22. The in-vivo device according to claim 14 wherein the device is to image the GI tract.

23. A system for displaying in-vivo images, the system comprising:
   an autonomous in-vivo imaging device comprising:
      an imager;
      an image data comparator, configured to determine similarity between captured image data and image data previously transmitted in a communication channel; and
      a transmitter to transmit image data, said transmitter configured to perform reduced transmissions of the image data if the captured image data is substantially similar to the image data previously transmitted in a communication channel, and if a quality level of the communication channel is above a pre-defined threshold value;
   a receiver; and
   an image display unit.

24. The system according to claim 23 wherein the in-vivo imaging device is to image the GI tract.

25. The system according to claim 23 wherein the transmitter is a RF transmitter.

26. The system according to claim 23 comprising a location detection system.

27. The system according to claim 23 wherein the transmitter is to transmit in a variable rate.

28. The system according to claim 23 wherein the image display unit is to display an image stream.

* * * * *